United States Patent [19]

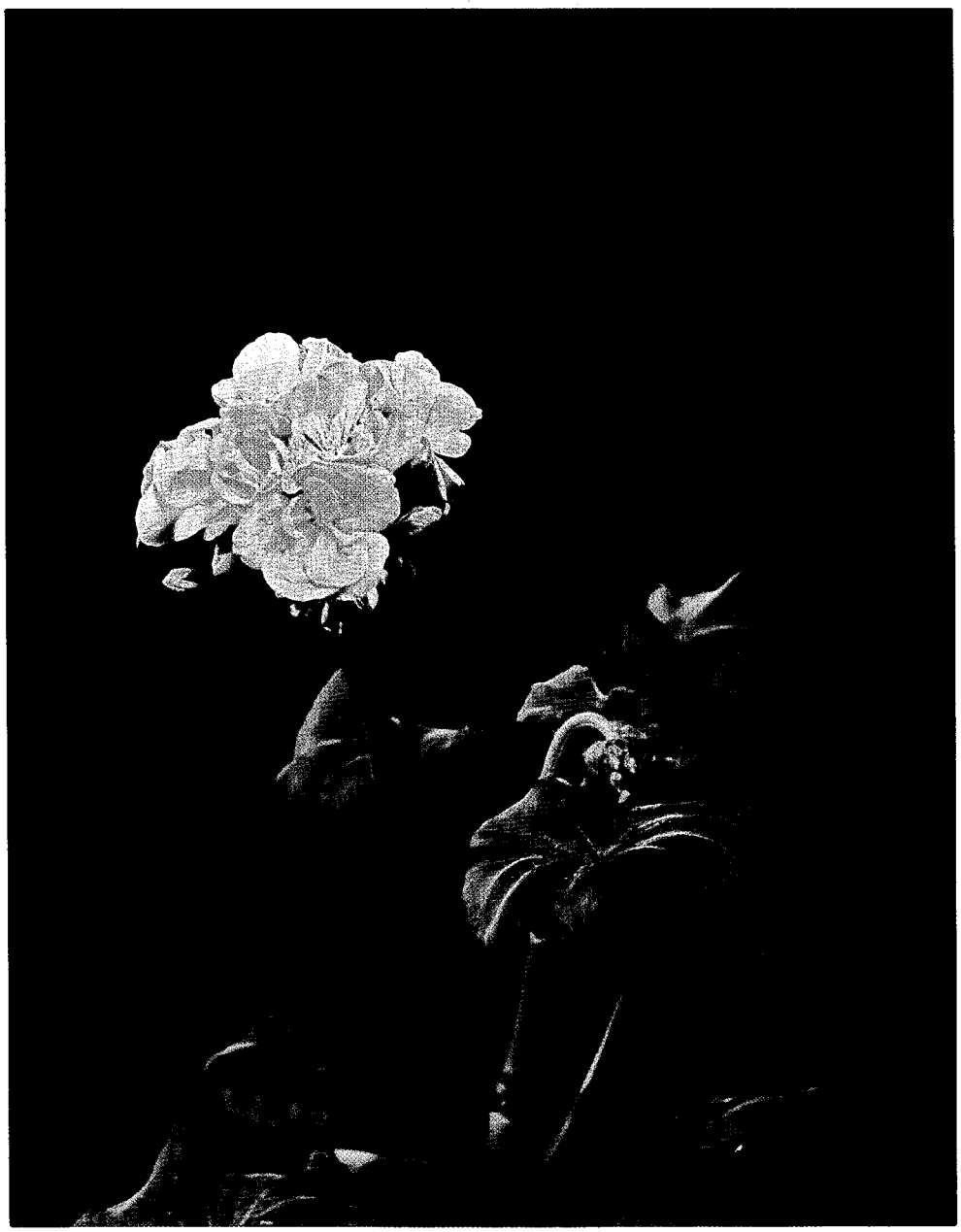

Buck

[11] Plant 4,040

[45] Apr. 12, 1977

[54] GERANIUM PLANT NAMED HAZEL

[75] Inventor: Griffith J. Buck, Ames, Iowa

[73] Assignee: Iowa State University Research Foundation, Inc., Ames, Iowa

[21] Appl. No.: 680,152

[22] Filed: May 3, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Rummler and Snow

[57] ABSTRACT

A new variety of geranium plant distinguished by the large size of its inflorescence and the large size of the florets, its capability to bloom throughout the year with adequate photoperiod, its tolerance of high summer night temperatures, and the intense smoky rose coloring of the flowers.

1 Drawing Figure

BACKGROUND OF THE NEW PLANT

This new geranium cultivar originated as a seedling produced by my crossing an unnamed variety in my stock, resulting from "Will Rogers" × "Pink Cloud" (both unpatented), as the seed parent, and the unpatented variety "Pink Jade" as the pollen parent, this work having been done during a continuous breeding program being carried on by me since 1956 at the Iowa State University Department of Agriculture at Ames, Iowa. This new cultivar was discovered by me in 1970 at Ames, Iowa, among the progeny of the said cross and was selected for propagation and test because of its abundant production of very large clusters of large sized florets and its very good tolerance of high night time temperature. Propagation of this new plant under my direction at Ames, Iowa, by means of cuttings, has been carried on through many generations which have clearly demonstrated that the distinctive characteristics of the plant hold true from generation to generation and are firmly fixed. Propagation of this plant is being continued at Ames, Iowa.

DESCRIPTION OF THE DRAWING

This new geranium plant is illustrated by the accompanying photographic drawing which shows blooms, buds and foliage of the plant in full color, the colors shown being as closely true as can be reasonably obtained by conventional professional photographic procedures.

DESCRIPTION OF THE NEW PLANT

The following is a detailed description of my new variety of geranium plant with the color designations according to Robert F. Wilson's Horticultural Colour Chart published by the Royal Horticultural Society at London, England, in collaboration with the British Colour Council, the following data being from observations of the new plant made at Iowa State University at Ames, Iowa.

THE PLANT

Origin: Seedling.

Parentage:

*Seed parent.*—An unnamed variety derived from "Will Rogers" (unpatented) × "Pink Cloud" (unpatented).

*Pollen parent.*—"Pink Jade" (unpatented).

Classification:

*Botanic.*—*Pelargonium hortorum*, Bailey.

*Commercial.*—Garden geranium.

Form: Bush.

Height: 30 to 45 cm.; 30 cm. as a 4 inch pot plant.

Growth: Vigorous, upright and branching.

Strength: Sturdy and very resistant to being broken apart by wind and rain.

Foliage: Quantity — abundant.

Leaves:

*Size.*—10 to 15 cm. in diameter.

*Shape.*—Round-cordate, with several rounded lobes and serrate margins.

*Texture.*—Leathery and firm to the touch.

*Aspect.*—Slightly pubescent.

*Color.*—Upper side — Indistinct center zone Spinach Green 0960 (HCC) in color with a somewhat darker periphery. Under side — Spinach Green 0960/2.

*Ribs and Veins.*—Conspicuous on the under side.

Petioles: 10.2 to 15 cm. long.

Stem: Aspect — Slightly hairy.

*Color.*—Scheeles Green 860/2 (HCC) maturing to Spinach Green 0960/2 (HCC).

*Internodes.*—Short — 1.3 to 1.7 cm. long.

Stipule: Triangular in shape and serrate at tip.

*Size.*—1.5 to 1.8 cm. long × 0.7 to 0.9 cm. wide.

*Color.*—Spinach Green 0960/2 (HCC).

*Aspect.*—Slightly hairy.

THE BUD

Size: Large; 1.2 to 1.6 cm. long × 0.6 to 0.8 cm. in diameter.

Shape: Pointed ovoid.

Opening: Bud opens slowly.

Color: When sepals first divide — Rose Red 724 (HCC). When petals begin to unfurl — Rose Bengal 25 (HCC).

Sepals: 5 separated sepals which curl back.

*Shape.*—Long ovoid-pointed.

*Color.*—Inside — Spinach Green 0960 (HCC) tinted with Rose Bengal 25 (HCC) at the base. Outside — Spinach Green 0960/2.

Calyx: Aspect — Slightly hairy.

THE FLOWER

Blooming Habit: Continuous through the year with adequate photoperiod.

Size: Very large. Diameter — 10 to 13 cm. Depth — 6 to 8 cm.

Borne: Inflorescence is an umbel and is borne singly.

Shape: Compact; somewhat globular.

Florets:

*Form.*—Flat to shallow cup-shape.

*Size.*—4.3 to 4.9 cm. in diameter.

*Petals.*—7 to 9 in number, including petaloids. Arrangement: Imbricate. Shape: Obovate to spatulate. Color: Upper side — Rose Bengal 25 (HCC), overlaid from white at base, changing to Spirea 025 (HCC) with age, high light intensities or high temperatures. Reverse side — Generally the same as upper side but color is less intense.

*Texture.*—Firm.

*Appearance.*—Satiny.

Petaloids: 0 to 3 in number.

*Size.*—1.1 to 1.5 cm. long.

*Shape.*—Spatulate.

*Color.*—Rose Bengal 25 (HCC).

Pedicel: 2.2 to 3 cm. long.

*Aspect.*—Slightly hairy.

*Color.*—Spinach Green 0960/2 (HCC) tinted Rose Bengal 25 (HCC).

Peduncle:

*Length.*—15 to 20 cm.

*Strength.*—Sturdy and upright.

Persistence: Flowers hang on and dry.

Disease Resistance: Plant is tolerant of *Botrytis cinerea.*

Lasting Quality: 7 days.

REPRODUCTIVE ORGANS

Stamens:

*Anthers.*—5 to 8 in number. Length: 0.3 cm. Arrangement: Cylindrical.

*Filaments.*—Length: 0.1 to 0.9 cm. Color: White.

*Pollen.*—Color — Brown.

Pistils:

*Number.*—1.

*Length.*—1.0 to 1.2 cm.

*Stigma.*—Color—Red.

Ovaries: 5 celled.

Fruit: Partially fertile.

*Shape.*—Ovoid with a long "beak".

*Color at Maturity.*—Brownish-black.

This variety of geranium plant is similar in color to the varieties "Galaxie" (unpatented) and "Penny" (Syn. "Penney Irene" — unpatented) but differs from those cultivars by its larger floret and larger inflorescence and its more intense smoky rose coloring. This plant is similar to "Galaxie" in its compact habit and tolerance of high summer night time heat and Botrytis cinerea but it is more floriferous than that cultivar and has the added potential to produce inflorescence consistently on a 2–4 node cycle.

I claim:

1. A new and distinct geranium cultivar substantially as herein shown and described, characterized by its abundant production of large umbel-form clusters of very large florets, the intense smoky rose coloring of its flowers, and its resistance to breakage by rain and wind.

* * * * *

UNITED STATES PATENT OFFICE

CERTIFICATE OF CORRECTION

Patent No. PP 4040 Dated April 12, 1977

Inventor(s) Griffith J. Buck

It is certified that error appears in the above-identified patent and that said Letters Patent are hereby corrected as shown below:

The drawing figure, as shown, should be deleted and substituted with the attached drawing figure therefor.

THIS CERTIFICATE APPLYS TO THE GRANT ONLY

Signed and Sealed this

*Twenty-second* Day of *November 1977*

[SEAL]

*Attest:*

RUTH C. MASON
*Attesting Officer*

LUTRELLE F. PARKER
*Acting Commissioner of Patents and Trademarks*